United States Patent [19]

Weissman

[11] Patent Number: 4,655,711
[45] Date of Patent: Apr. 7, 1987

[54] PLACEMENT ASSEMBLY FOR A DENTAL PIN

[75] Inventor: Bernard Weissman, New York, N.Y.

[73] Assignee: Ipco Corporation, White Plains, N.Y.

[21] Appl. No.: 865,280

[22] Filed: May 21, 1986

[51] Int. Cl.⁴ .............................................. A61C 5/04
[52] U.S. Cl. .................................................. 433/225
[58] Field of Search ................................ 433/225, 165

[56] References Cited

U.S. PATENT DOCUMENTS

4,337,043  6/1982  Weissman ............................ 433/225
4,365,958  12/1982  Vlock ................................... 433/225

Primary Examiner—Robert Peshock
Attorney, Agent, or Firm—Goodman & Teitelbaum

[57] ABSTRACT

A placement assembly which is received in a dental handpiece and is utilized for insertion of a threaded dental pin into a preformed bore in a tooth. The assembly includes an elongated manipulating body portion with the dental pin projecting from an operating end of the body portion. A shank is frangibly coupled to a driving end of the body portion for driving engagement with the dental handpiece to thread the dental pin into the bore. The shank automatically severs from the body portion prior to the final seating of the dental pin in the bore. The body portion is utilized as a hand tool for the final seating of the dental pin in the bore. The body portion is then disengaged from the dental pin to leave the dental pin properly seated in the bore.

23 Claims, 40 Drawing Figures

PLACEMENT ASSEMBLY FOR A DENTAL PIN

BACKGROUND OF THE INVENTION

This invention relates to dentistry, and more particularly to a placement assembly for the insertion of a dental pin into a preformed bore in a tooth stub.

Dental pins are frequently utilized in dental procedures. The dental pin generally includes a threaded post with an enlarged head. The threaded post is threaded into a preformed bore in a tooth stub with the enlarged head projecting above the surface of the tooth stub. A dental superstructure such as a crown, replacement tooth, or the like, is then secured onto the tooth stub utilizing the enlarged head for retaining the superstructure on the tooth stub. Other purposes for such dental pins are also well known in the field of dentistry.

Various insertion devices are available for threading the dental pin into the preformed bore in the tooth stub. One method involves utilizing a hand driver. Other methods utilize a handpiece connected to an automatic drill head or other rotating mechanism. Because the dental pins are of exceedingly small size, there is frequently included an additional retaining portion for holding the dental pin, and the retaining portion is then manipulated by means of the hand driver or automatic handpiece. A dental tool having one such retaining portion is described in my U.S. Pat. No. 4,255,145, issued on Mar. 10, 1981 for a "Dental Tool Having Severable Sections". In that patent, there is disclosed a dental tool provided with a retaining portion having at least two sections with each section including an individual latching arrangement. The sections are so arranged that they can be separable to conveniently provide a desired length for the dental tool to fit into the operative areas of the patient's mouth.

Although the foregoing insertion systems for dental pins have been useful, extreme care must be extended with such systems to provide appropriate seating of the dental pin in the bore. When utilizing automatic handpieces, there is a tendency of overthreading the dental pin, thereby inserting the pin to a greater depth than the preformed bore. Additional stress is then placed on the tooth stub by such excessive threading. Thus, the tooth stub may crack, or the dental pin may snap, or other dangerous situations can occur. Although the use of the automatic handpiece is convenient, it becomes difficult to adequately control the handpiece in order to provide a desired seating of the dental pin in the preformed bore.

On the other hand, the use of a hand driver to manually insert the dental pin may achieve better control, but is a difficult task both for the patient and for the dentist. The process is slow, requiring excessive strain on the patient who must maintain his position for an extended length of time. It is also a difficult task for the dentist who must operate at a continuous methodical pace driving the dental pin throughout the depth of the preformed bore. Such slow process often causes angular distortions and failure to properly position the dental pin with sufficient accuracy.

Accordingly, while dental pins have found an important role in various dental procedures, there is still needed an adequate placement system for approximately seating the dental pin in the preformed bore of the tooth stub.

SUMMARY OF THE INVENTION

Accordingly, it is an object of the present invention to provide a placement system for dental pins.

Another object of the present invention is to provide a placement assembly for a dental pin which permits automatic course adjustment and manual fine adjustment for threading the pin into a tooth bore.

Yet a further object of the present invention is to provide a pin placement assembly which utilizes an automatic handpiece for initial insertion of the dental pin into a preformed bore provided in the tooth, and further permits manual final seating of the dental pin to a desired position within the bore.

Another object of the present invention is to provide a pin placing system formed of a unitary assembly, for use both in the initial placement of the dental pin as well as the final adjustment of the dental pin.

Still a further object of the present invention is to provide a pin placement assembly which is utilized for proper placement of a dental pin in a preformed bore and which is disposable after use.

Yet another object of the present invention is to provide a pin placement assembly which permits accurate placement of a dental pin in a preformed bore of a tooth, while permitting such placement with speed, minimal manipulation, and reduced strain on the patient's tooth.

The foregoing objects are achieved in accordance with the present invention, wherein there is provided a placement assembly which is receivable in a dental handpiece and is utilized for the threaded insertion of a dental pin into a preformed bore in a tooth stub. The placement assembly includes a central elongated manipulating body portion. The dental pin is projectingly supported from an operating end of the body portion for threading into the bore. A disengaging interconnection is provided between the body portion and the dental pin, whereby the body portion can be easily disengaged from the dental pin upon the final seating of the dental pin in the bore. A shank is frangibly coupled to a driving end of the body portion for driving engagement with a dental handpiece, thereby initially threading the dental pin into the bore. The shank automatically severs from the body portion when sufficient stresses are built up during partial insertion of the dental pin into the bore, which is prior to the final seating of the dental pin. At this point, the body portion can be manually manipulated to achieve the final seating of the dental pin. The body portion can then be disengaged from the dental pin, thus leaving the dental pin inserted into the bore.

In an embodiment of the invention, the elongated manipulating body portion and the body portion and the shank portion are integrally formed of plastic material, with a metallic dental pin being embedded into the operating end of the body portion. The dental pin is securely embedded by the presence of an annular shoulder provided at the distal operating end of the body portion for retaining an enlarged head of the dental pin within the operating end. The annular shoulder is deformed upon application of an axial disengaging force, thereby releasing the dental pin from the body portion and permitting the retention of the dental pin in the bore, and also permitting the disposal of both the severed shank portion and the manipulating body portion.

In another embodiment, the enlarged head includes a flat tang which is held within a bifurcated prong either by a frictional engagement, or by means of a collar which slides onto the prong and forces the legs of the prong together onto the tang.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of preferred embodiments, in which.

In the various figures of the drawing, like reference numerals designate like parts.

DETAILED DESCRIPTION OF THE PREFERRED EMBODIMENTS

Figure 1:
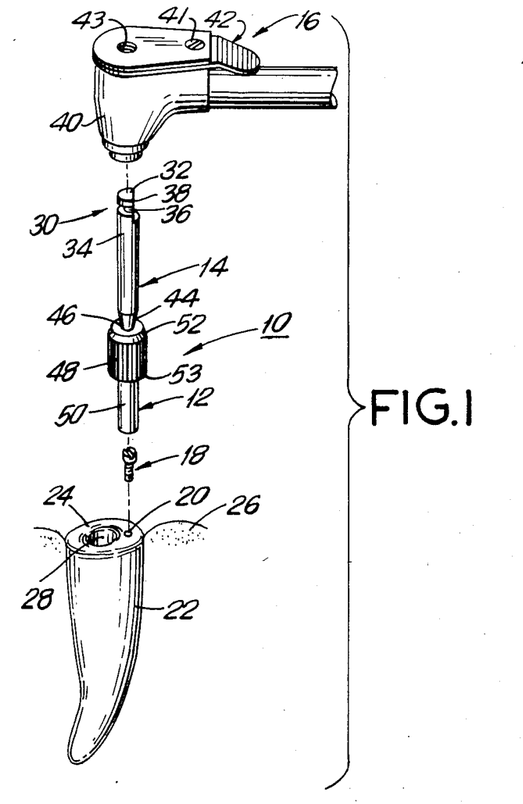
FIG. 1 is an exploded perspective view of a placement assembly according to the present invention, which is receivable in a dental handpiece for inserting of a dental pin into a preformed bore in a tooth stub.

Referring now to FIG. 1, the placement assembly of the present invention is shown generally at 10, and includes a central elongated manipulating body portion 12 which integrally depends from a driving shank portion 14 in a one piece construction. The shank portion 14 is receivable within a conventional handpiece 16 for driving engagement. Embedded into an end of the manipulating body portion 12, and projecting therefrom, is a dental pin 18 which completes the placement assembly 10. The dental pin 18 is to be inserted into a preformed bore 20 provided within a prepared tooth stub 22, as set forth below.

Typically, a tooth may have been cracked, damaged or the like, and will be filed down to the tooth stub 22 to provide an upper surface 24 proximate the gum level 26. The central root may be removed from the root canal 28, and at least one or more bores 20 are provided into the surface 24 for receiving the dental pin or pins 18. The dental pins 18 must be properly seated into the bores 20 with at least a portion of the dental pin 18 projecting above the surface 24 onto which a superstructure can be erected in a manner well known in the dental art.

The shank portion 14 has a right angle latch drive 30 at its upper end including a head flange 32 separated from a cylindrical body 34 by a reduced diameter neck 36. One side 38 of the head flange 32 is flattened with the flat side 38 extending down along the neck 36 and into a part of the cylindrical body 34.

The right angle latch drive 30 is received within an aperture in the head 40 of the conventional handpiece 16. One end portion of the manipulating thumb lever 42 is notched (not shown) to engage, when pivoted about the screw 41, the reduced diameter neck 36 of the latch drive 30 to retain the shank portion 14 in the handpiece 16, with the head flange 32 extending into the hole 43 in the handpiece 16. A corresponding flattened surface within the handpiece engages the flat side 38 for driving engagement of the shank portion 14. For further details of the right angle latch drive, reference is made to U.S. Pat. No. 4,255,145.

The shank portion 14 is interconnected to the manipulating body portion 12 by means of an inwardly tapered section 44 integral with the shank portion 14 and terminating in a reduced diameter frangible throat 46 provided at the upper end of the shank portion 14. This permits shearing upon excess of rotational stresses between the shank portion 14 and the manipulating body portion 12.

The manipulating body portion 12 includes an enlarged upper substantially cylindrical section 48 having a peripheral knurl to provide a knob for use as a hand driver unit. A thinner elongated cylindrical stem portion 50 integrally depends from the knob 48. The upper end 52 of the knob 48 is preferably chamferred, where the lower end 53 may also be chamferred.

Figure 2:
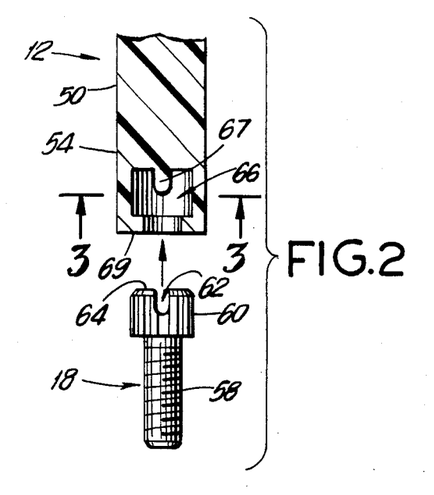
FIG. 2 is an exploded fragmented cross sectional view, showing the dental pin for insertion within the operating end of the body portion of the placement assembly in accordance with a first embodiment of the dental pin shown in FIG. 1.
Figure 3:
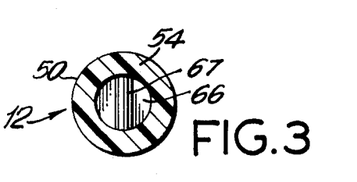
FIG. 3 is a cross sectional view taken along line 3—3 of FIG. 2.
Figure 4:
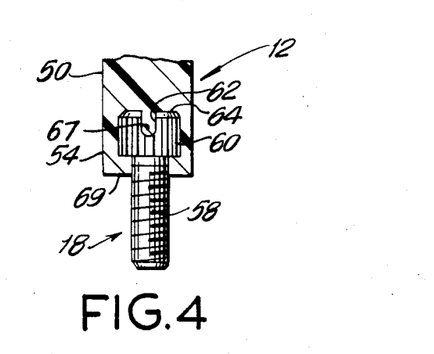
FIG. 4 is a fragmented sectional view showing the dental pin of FIG. 2 embedded into the operating end of the body portion.

Referring now to FIGS. 2-4, there is shown an enlargement of the coupling between the dental pin 18 and the body portion 12. As shown in FIG. 2, at the lower operating end 54 of the stem portion 50 of the body portion 12, there is to be inserted the dental pin 18. The dental pin 18 includes a peripherally threaded post 58 with an enlarged head 60. The head 60 is slotted with a transverse slot 62 formed into the upper surface 64 of the head 60.

Formed into the operating end 54 is a seat 66 having a complementary mating shape to the pin head 60. As best shown in FIGS. 3 and 4, the dental pin 18 is embedded into the operating end 54 whereby a driving tang portion 67, extending into the seat 66, matingly corresponds to the slot 62 for engaging and rotating the dental pin 18. An annular peripheral shoulder 69 is provided beneath the pin head 60 to retain the pin head 60 within the seat 66 of the operating end 54.

Typically, the shank portion 14 and manipulating body portion 12 can be integrally formed of a one piece construction, being fabricated from a plastic material. The dental pin 18, which can be metal, can be directly inserted into the operating end 54 of the manipulating body portion 14 to provide a mating seat portion for retention of the dental pin head 60, so that the enlarged head 60 of the dental pin 18 can be driven by the body portion 12. Alternatively, the shank and body portions 14, 12 can be molded onto the head 60 of the dental pin 18.

Figure 5:
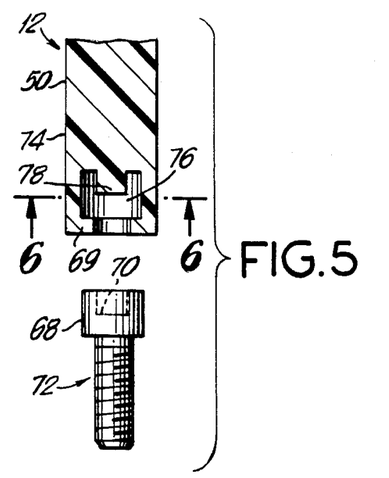
FIG. 5 is an exploded fragmented cross sectional view similar to FIG. 2, showing a second embodiment of a socket-type head of a dental pin for insertion into a corresponding mating seat portion of an operating end of a body portion.
Figure 6:
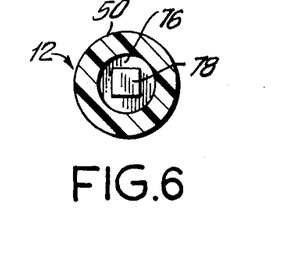
FIG. 6 is a cross sectional view taken along line 6—6 of FIG. 5.
Figure 7:
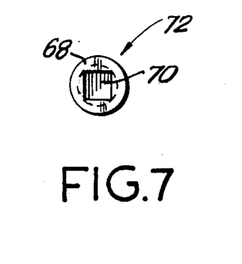
FIG. 7 is a top view of the dental pin of FIG. 5.

Referring to FIGS. 5-7 another embodiment of a threaded dental pin is shown, wherein the modified dental pin 72 includes a socket head 68 with a substantially square socket 70 recessed within the head 68. The pin 72 is embedded into a modified operating end 74 of the stem portion 50 of the body portion 12 having a seat 76 matingly corresponding in shape and including a square driving socket member 78 which is used to drive the dental pin 72 in the same manner as set forth above.

Figure 8:
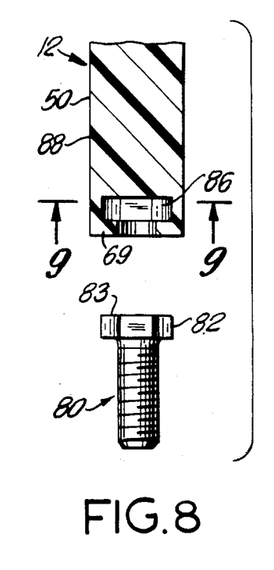
FIG. 8 is an exploded fragmented cross sectional view similar to that shown in FIG. 2, showing a third embodiment of a hex head dental pin for insertion into a corresponding mating seat portion of an operating end of a body portion.
Figures 9, 10, 11:
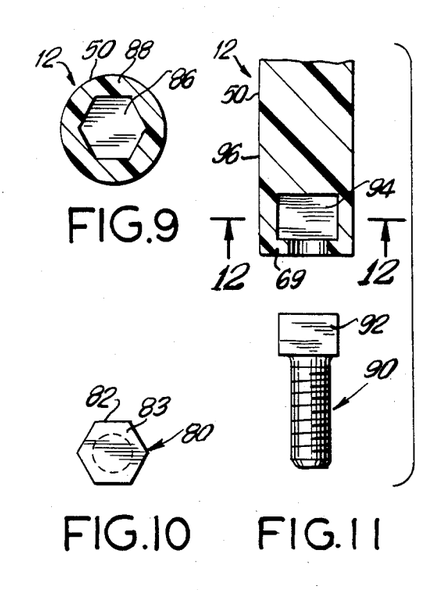
FIG. 9 is a cross sectional view taken along line 9—9 of FIG. 8.
FIG. 10 is a top view of the dental pin of FIG. 8.
FIG. 11 is an exploded fragmented cross sectional view similar to that shown in FIG. 2, showing a fourth embodiment of a dental pin having a square head for insertion into a corresponding mating seat portion of an operating end of a body portion.

As shown in FIGS. 8-10, a modified threaded dental pin 80 includes a hexagonal shaped head 82 having a substantially flat upper surface 83. A mating hexagonal seat 86 is provided in a modified operating end 88 of the stem portion 50 of the body portion 12 for driving the dental pin 80 in the manner set forth above.

Figure 12:
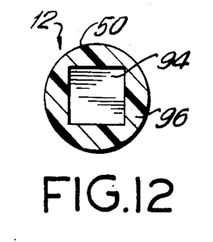
FIG. 12 is a cross sectional view taken along line 12—12 of FIG. 11.
Figure 13:
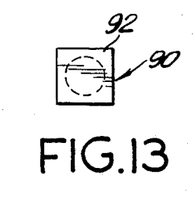
FIG. 13 is a top view of the dental pin of FIG. 11.

FIGS. 11-13 show an alternate embodiment where the modified threaded dental pin 90 includes a square head 92 to be received in a square seat 94 in the modified operating end 96 of the stem portion 50 of the body portion 12 for driving the dental pin 90 in the manner set forth above.

Figure 14:
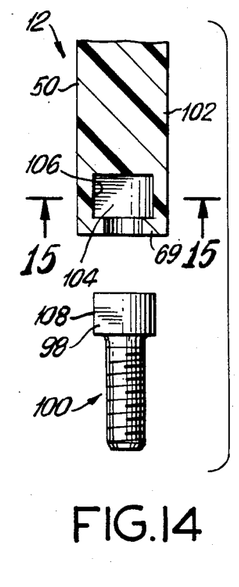
FIG. 14 is an exploded fragmented cross sectional view similar to that shown in FIG. 2, showing a fifth embodiment of a dental pin having a D-shaped head for insertion into a corresponding mating seat portion of an operating end of a body portion.
Figures 15, 16, 17:
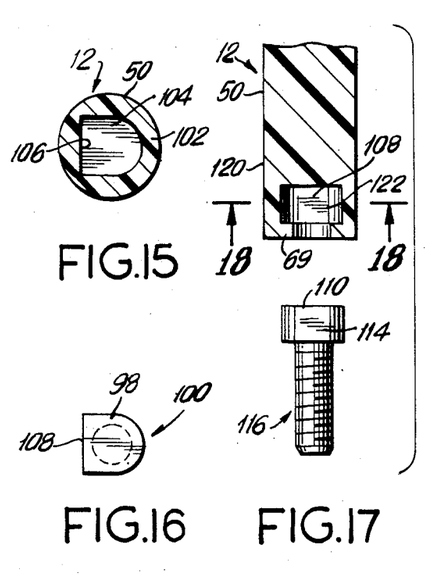
FIG. 15 is a cross sectional view taken along line 15—15 of FIG. 14.
FIG. 16 is a top view of the dental pin shown in FIG. 14.
FIG. 17 is an exploded fragmented sectional view similar to that shown in FIG. 2, showing a sixth embodiment of a dental pin having a double-D head arrangement with opposing flattened sides for insertion into a corresponding mating seat portion of an operating end of a body portion.

Other shaped head arrangements can be included, such as that shown in FIGS. 14-16, where the enlarged pin head 98 has a D-shaped configuration. The modified threaded dental pin 100 is embedded into the modified operating end 102 of the stem portion 50 of the body portion 12 having a correspondingly shaped seat 104 including a flattened side surface 106 which can drivingly engage the flattened side 108 of the pin head 98 for driving the dental pin 100 in the manner set forth above.

Figure 18:
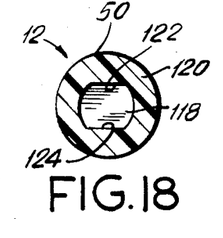
FIG. 18 is a cross sectional view taken along line 18—18 of FIG. 17.
Figure 19:
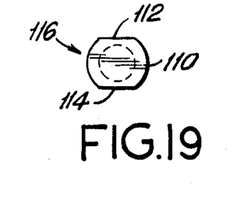
FIG. 19 is a top view of the dental pin shown in FIG. 17.

A double D-shaped arrangement can also be formed as shown in FIGS. 17-18. The double D-shaped arrangement of the pin head 110 includes opposing flattened sides 112, 114. The modified threaded dental pin 116 is inserted into a seat 118 in the modified operating end 120 of the stem portion 50 of the body portion 12 with the seat 118 having a mating double D-shaped configuration including opposing flattened sides 122, 124. The opposing sides 122, 124 can drivingly engage the dental pin sides 112, 114 for driving the dental pin 116 in the manner set forth above.

Figure 20:
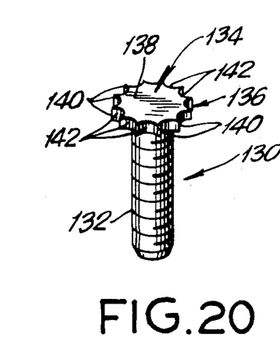
FIG. 20 is a perspective view of a modified dental pin in accordance with a further embodiment of the present invention.

FIG. 20 shows another embodiment of a modified dental pin 130 having a threaded post 132 with an enlarged head 134, the head 134 having peripheral scallops formed thereabout. The top surface 138 of the head 134 is flat. The scalloped periphery 136 includes crest portions 140 separated by recesses 142, equally spaced about the periphery of the head 134.

Figure 21:
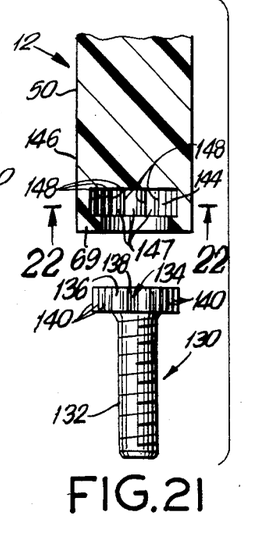
FIG. 21 is an exploded fragmented cross sectional view similar to that shown in FIG. 2, showing the dental pin of FIG. 20 for insertion into a corresponding mating seat portion of a modified operating end of a body portion.
Figure 22:
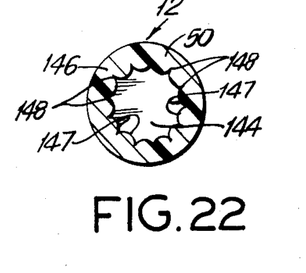
FIG. 22 is a cross sectional view taken along line 22—22 of FIG. 21.
Figure 23:
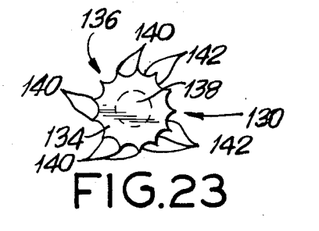
FIG. 23 is a top view of the dental pin shown in FIG. 20.

The head 134 is inserted into a seat 144 in the modified operating end 146 of the stem portion 50 of the body portion 12 corresponding in shape to that of the scalloped head 134. The seat 144 has a periphery of scallops including ridges 147 separated by indents 148. The indents 148 would receive the crests 140 of the enlarged head 134 to drive the dental pin 130.

Figure 24:
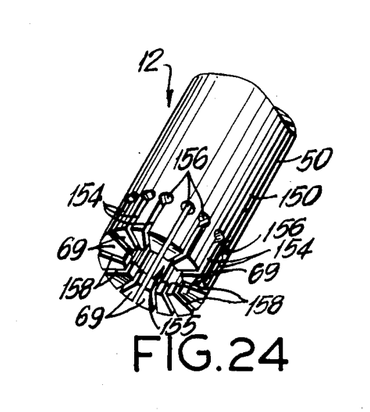
FIG. 24 is a fragmented perspective view, showing a slotted operating end of a body portion in accordance with another embodiment of the present invention which facilitates disengagement of the dental pin of FIG. 20 from the body portion.
Figure 25:
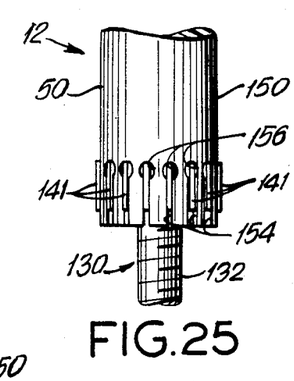
FIG. 25 is a fragmented side elevational view, showing the dental pin of FIG. 20 inserted into the operating end of FIG. 24.
Figure 26:
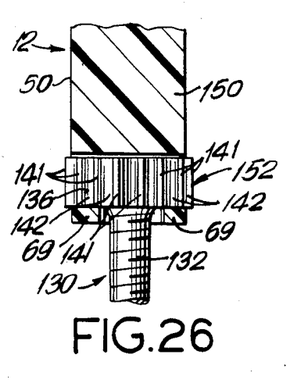
FIG. 26 is a fragmented cross sectional elevational view taken through the embodiment shown in FIG. 25.

FIGS. 24–26 show an alternate arrangement of a modified operating end 150 of the stem portion 50 of the body portion 12 which can accommodate a modified head 152 of the dental pin 130 shown in FIG. 20. At the operating end 150 there are provided a plurality of axial slots 154 radially disposed about the lower distal end of the body portion 12 and extending into a seat 155. The slots 154 terminate at enlarged holes 156 at the upper ends thereof, and continue downwardly into the bottom radial slots 158 along the lower edge. The crest portions 141 of the peripheral head 152 are received within the slots 154, where the head 152 has a larger diameter than the head 134 of FIG. 20.

The head 152 is received in the seat 155 in the operating end 150 so that the crest portions 141 extend outwardly through the slots 154, the crest portions 141 extending slightly beyond the periphery of the operating end 150 as shown in FIG. 25.

In each of the above embodiments, where the enlarged head is seated in the operating end of the body portion, a part of the body portion disposed beneath the head forms shoulders 69 which retain the enlarged head in the body portion. After insertion of the pin into the tooth, when disengaging the dental pin from the body portion, the shoulder portions 69 are bent or fractured, as set forth below. In the operating end of FIGS. 24–26, the individual sections between the slots 154 are spread apart when the enlarged head is extracted from the seat 155 causing the shoulders 69 to bend away from each other.

Figure 27:
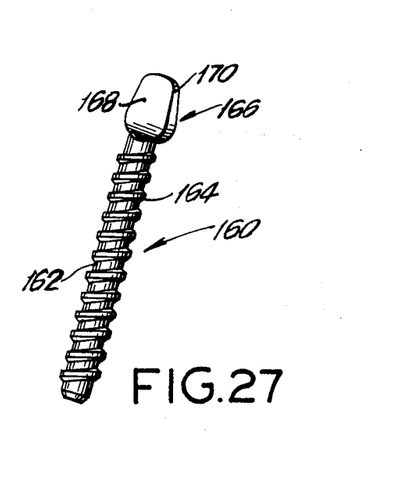
FIG. 27 is a perspective view of a dental pin in accordance with a further embodiment of the present invention.

FIG. 27 shows another dental pin 160 having a cylindrical post 162 with a surrounding spiral thread 164. At the upper end is provided an enlarged head 166 in the form of a flattened tang having opposing sides 168, 170. The head 166 is upwardly tapered to have a narrow upper edge. The head 166 has a substantially oval shape.

Figure 28:
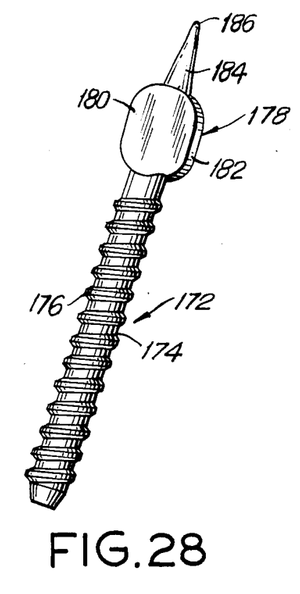
FIG. 28 is a perspective view of a dental pin in accordance with a still further embodiment of the present invention.

FIG. 28 shows a dental pin 172 having a cylindrical post 174 with a surrounding spiral thread 176. The upper end terminates in an enlarged head 178 in the form of a flattened tang having opposing flat surfaces 180, 182. The head 178 is substantially oval shaped and terminates in an upwardly directed conical tip 184 having a slightly rounded upper end 186.

Figure 29:
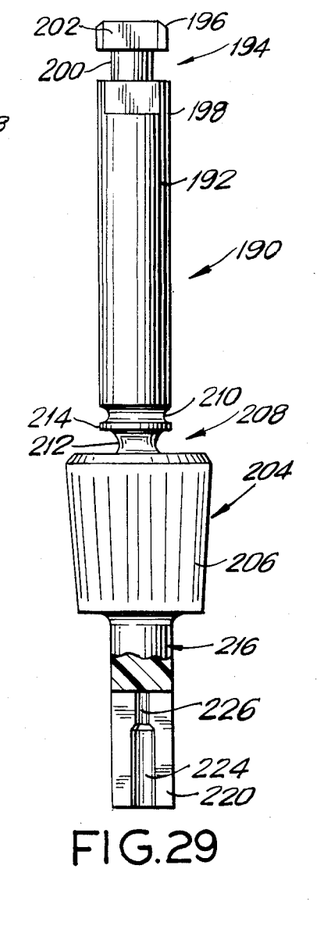
FIG. 29 is an elevational view, partly cut away, of a further modified placement assembly for use with the dental pins of FIGS. 27 and 28.
Figure 30:
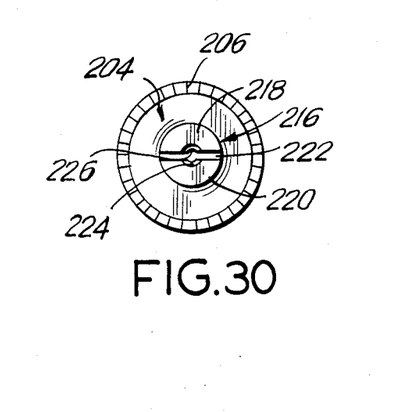
FIG. 30 is an end view of the placement assembly shown in FIG. 29.

A one-piece placement assembly holder 190 for use with the dental pins 160, 172 of FIGS. 27 or 28 is shown in FIG. 29. The placement assembly holder 190 includes an upper driving shank portion 192 terminating at its upper distal end with a right angle latch drive 194 similar to that heretofore described, including an upper head flange 196 separated from the cylindrical body 198 by means of a reduced diameter neck 200. One side 202 of the latch drive 194 is flattened, in the manner set forth above.

Separated from the shank portion 192 is an enlarged manipulating body portion 204 having a downwardly tapered section 206 having a peripheral knurl. The interconnection between the shank portion 192 and the manipulating body portion 204 is a frangible section 208. The frangible section 208 includes an annular groove 210 separated from a smaller diameter annular throat 212 by means of a flanged collar 214. Upon application of excess rotational stresses between the shank portion 192 and the manipulating body portion 204, the reduced diameter annular throat 212 will permit shearing of the frangible section 208 to separate the manipulating body portion 204 from the shank portion 192.

The manipulating body portion 204 terminates in a cylindrical stem portion 216 having its lower part bifurcated to provide a pair of opposing legs 218, 220. The slot 222 separating the legs 218, 220 includes a cylindrical bore 224 terminating at its upper inner end in a reduced diameter aperture 226.

Figure 31:
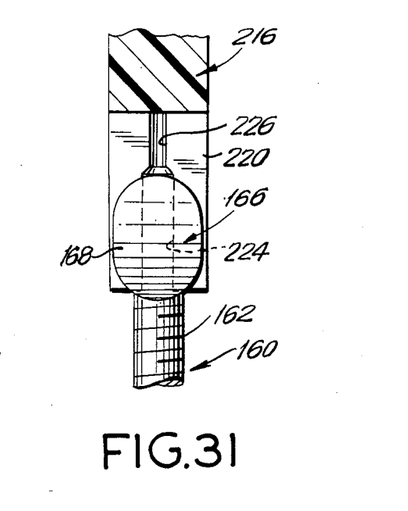
FIG. 31 is a fragmented cross sectional view taken through the operating end of the placement assembly of FIG. 29, showing the dental pin of FIG. 27 inserted into the operating end.

The dental pin 160 of FIG. 27 can be retained within the placement assembly holder 190 of FIG. 29, as shown in FIG. 31. The flattened tang head 166 is held within the slot 222 between the bifurcated legs 218, 220, being retained by means of a friction fit caused by the tapered head 166 when wedged into the slot 222. The opposing legs 218, 220 are utilized to manipulate the dental pin 160 for threading into the tooth.

Figure 32:
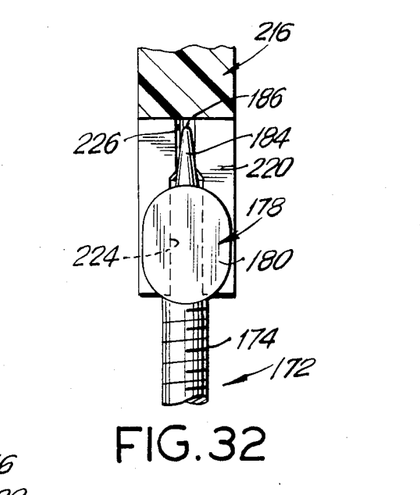
FIG. 32 is a fragmented cross sectional view similar to that shown in FIG. 31, showing the dental pin of FIG. 28 inserted into the operating end of the placement assembly of FIG. 29.

The dental pin 172 of FIG. 28 can also be manipulated by the placement assembly holder 190 of FIG. 29, as shown in FIG. 32. In this case, in addition to the tang head 178 being frictionally retained between the bifurcated legs 218, 220, the conical tip 184 is wedged into the upper reduced diameter aperture 226. Here again, the opposing legs 218, 220 manipulate the dental pin 172 for threading into the tooth.

Figure 33:
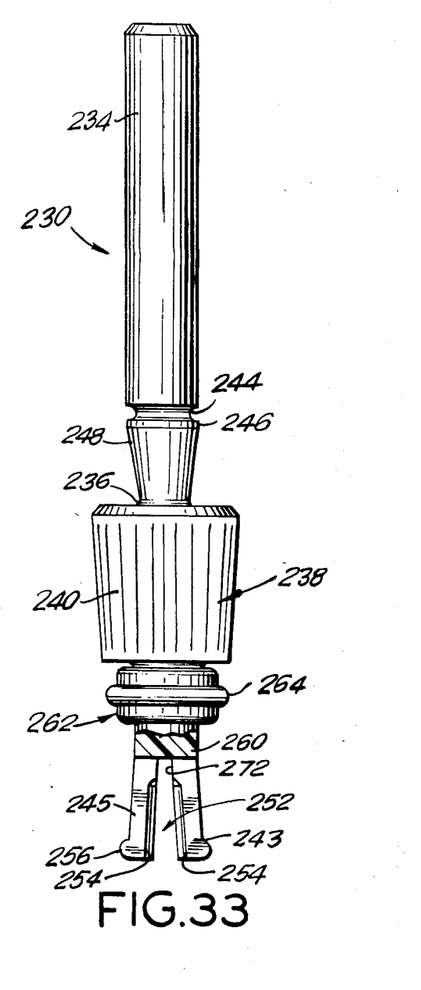
FIG. 33 is an elevational view, partly cut away, of a still further modified placement assembly similar to that shown in FIG. 29.
Figure 34:
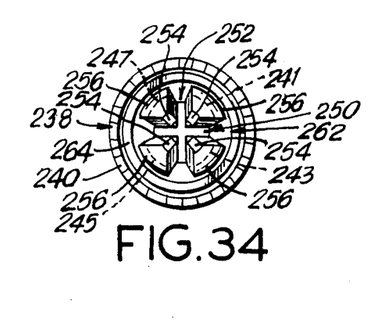
FIG. 34 is an end view of the placement assembly of FIG. 33.

FIG. 33 shows another placement assembly holder 230 which can also be utilized for proper placement of the dental pins 160, 172 of FIGS. 27 and 28. The placement assembly holder 230 includes a driving shank portion 234 which is frictionally held in a conventional friction handpiece well known in the dental art for driving engagement. A reduced diameter throat portion 236 separates the shank portion 234 from the enlarged manipulating body portion 238. The body portion 238 has a slight downward taper and includes a peripheral knurled surface 240. The shank portion 234 includes an annular groove 244 with a lower collar portion 246 extending into a slightly downwardly tapered section 248 of the shank portion 234.

Downwardly depending from the manipulating body portion 238 are outwardly flaring quadralateral legs 241, 243, 245, 247 which extend away from each other. The four legs are separated by means of cross slots 250, 252. Each of the legs is a quarter circle sector in cross section having an arcuate inner surface 254. The arcuate surfaces 254 define a central bore which extends into a reduced diameter hole 272 at its upper end. The distal ends of the legs terminate in outwardly directed foot portions 256.

The four legs extend downwardly from a cylindrical stem portion 260 connected to the body portion 238. Around the stem portion is a separate annular collar 262 having an enlarged center grasping rim 264. The annular collar 262 is slidable along the stem portion 260 and moves down onto the quadralateral legs 241, 243, 245, 247 to compress them together.

Figure 35:
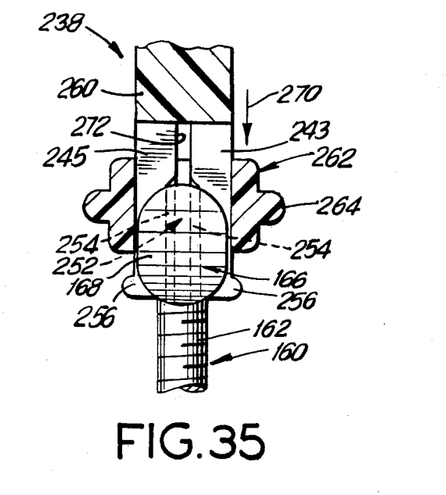
FIG. 35 is a fragmented cross sectional view of the operating end of the placement assembly shown in FIG. 33, showing the dental pin of FIG. 27 inserted into the operating end.

As shown in FIG. 35, the dental pin 160 of FIG. 27 is inserted into one of the slots 250, 252, being shown in slot 250 where it separates a first pair of bifurcated legs 241, 247 from the other pair of bifurcated legs 243, 245. The annular collar 262 is then slid downwardly, as shown by the arrow 270, to clamp together the quadralateral legs thereby locking the tang head 166 in place. The placement assembly holder 230 can then be utilized to threadingly manipulate the dental pin 160 into the bore in the tooth.

Figure 36:
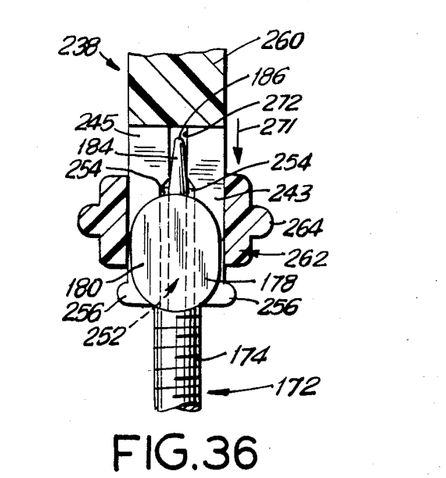
FIG. 36 is a fragmented cross sectional view similar to that shown in FIG. 35, showing the dental pin of FIG. 28 inserted into the operating end of the placement assembly of FIG. 33.

FIG. 36 shows the same arrangement with the dental pin 172 of FIG. 28. The tang head 178 is inserted between pairs of bifurcated legs. At the upper end of the slots, the hole 272 receives in wedging engagement the conical tip 184 to help position and secure the dental pin 172 in place. The collar 262 is then slid downwardly as shown by the arrow 271 to lock the tang head 178 in place to be threaded into the tooth.

Referring now to FIGS. 37-40, the operation of the present placement assembly will be best understood in that, by way of example, the embodiment of FIG. 1 will be used for the explanation thereof. Initially, the assembly 10 comprises three sections including the shank portion 14, the manipulating body portion 12 and the dental pin 18. The bore 20 is formed into the surface 24 of the tooth stub 22 of proper depth to accommodate the dental pin 18. The shank portion 14 is inserted into the handpiece 16 which automatically threads the dental pin 18 into the bore 20. The dental pin 18 has self threading threads so that the bore 20 is not tapped.

Figures 37, 38:
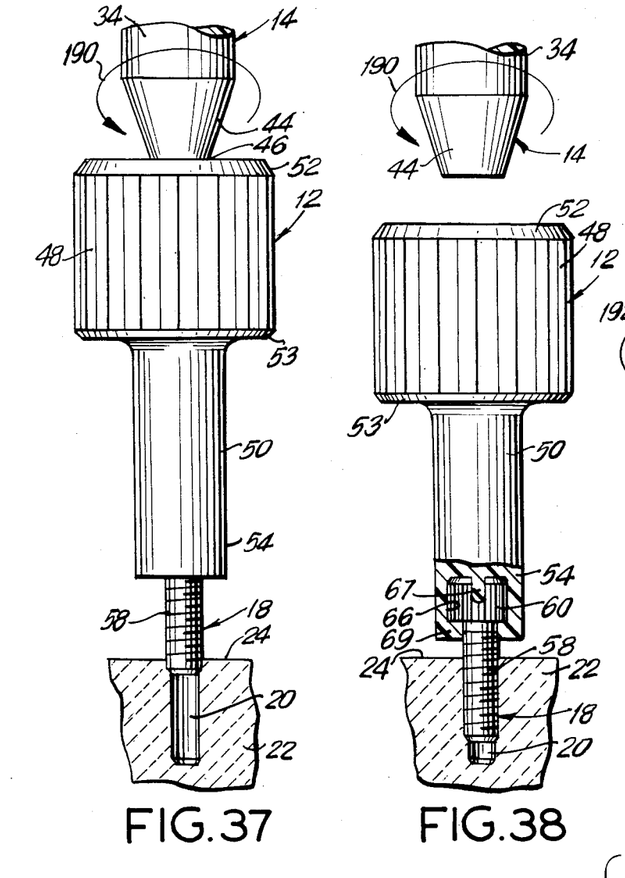
FIG. 37 is a fragmented side elevational view showing a first step in the insertion of the dental pin into a preformed bore in the tooth stub, specifically showing the initial insertion of the dental pin by the handpiece.
FIG. 38 is a fragmented view similar to that shown in FIG. 37, showing the severing of the shank portion at its frangible throat after partial insertion of the dental pin causes adequate stresses to sever the shank portion.
Figure 39:
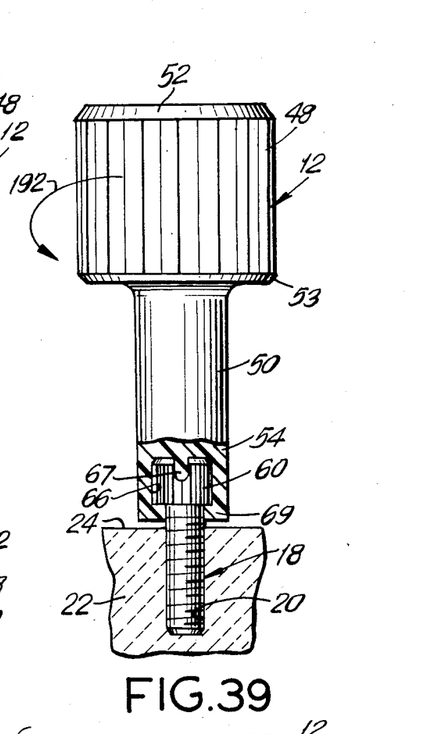
FIG. 39 is a fragmented view similar to that shown in FIG. 38, showing the use of the body portion as a manual hand driver for the final seating of the dental pin in the preformed bore of the tooth.

As the handpiece 16 rotates the placement assembly 10, it provides for the initial threading insertion of the dental pin 18 into the bore 20, as shown by the arrow 190. The threading continues, and as it does, the rotational pressure between the dental pin 18 and the tooth increases. As shown in FIG. 38, after partial insertion of the dental pin 18 into the bore 20, sufficient pressure has been built up so as to sever the shank portion 14 from the manipulating body portion 12 at the throat 46. The frangible throat 46 is of a size to sever as the pressure builds up to a predetermined point during the threading of the dental pin 18, however this predetermined point is reached prior to its final seated insertion in the bore 20.

With the shank portion 14 separated, the manipulating body portion 12 can now be utilized as a hand driver for the final seating of the dental pin 18 in the bore 20. The knurled knob 48 facilitates rotation of the body portion 12, as shown by arrow 192 in FIG. 39. By means of the manual rotation, the dentist can feel the proper amount of tension required for the seating insertion of the dental pin 18, thus providing the fine adjustment of the dental pin 18 to complete its final seating to a desired depth in the bore 20.

Figure 40:
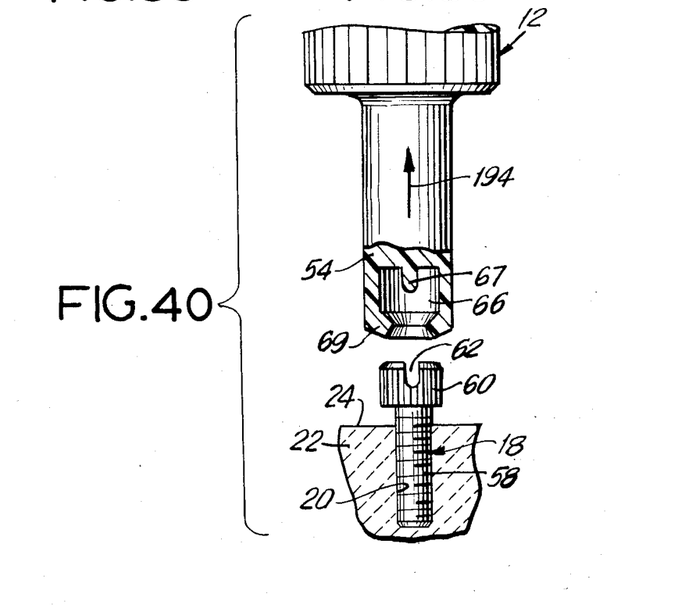
FIG. 40 is a fragmented view similar to that shown in FIG. 39, partially broken away, showing an axial force disengaging the body portion from the dental pin and leaving the dental pin inserted in the preformed bore.

After the dental pin 18 has been properly seated in the bore 20, the body portion 12 is pulled upwardly, as shown by the arrow 194 in FIG. 40, to disengage the body portion 12 from the dental pin 18. The disengagement occurs as the annular shoulder 69 at the bottom of the operating end 54 deforms, so as to permit release of the enlarged head portion 60 of the dental pin 18. After disengagement, the dental pin 18 remains seated in the tooth for use in building a dental superstructure onto the tooth stub 22 in a manner well known in the dental art.

It should be appreciated that with the present placement assembly, the dental handpiece is utilized for the initial insertion providing the course adjustment of the dental pin. The fine adjustment, and the ultimate final seating, is accomplished by means of the manipulating body portion serving as a hand driver.

The disengagement by deforming the retaining shoulder 69 under the dental pin 130 is facilitated when using the slotted end 150, as shown in FIGS. 24-26, which permits the slotted end 150 of the body portion 12 to flex outwardly thereby releasing the enlarged head 152 of the dental pin 130. However, the placement assembly holders 190, 230 of FIGS. 29 and 33 provide for disengagement without fracture or deformation of the body portions 204, 238 where the body portion 204 of FIG. 29 is merely pulled up for disengagement, and the collar 262 of the body portion 238 of FIG. 33 is first slid upwardly on the stem portion 260 and then the body portion 238 is pulled up for disengagement.

The entire placement assembly holder is disposable so that after the shank portion is severed and the body portion is disengaged, they can both be discarded. The entire placement assembly holder can be formed of plastic or the like material, where the dental pin is preferably metal. Although specifically shown as being seated within the body portion, it should be appreciated that the dental pin can actually be integrally formed of unitary construction with the placement assembly holder, while being frangibly separable from the body portion.

By means of the present placement assembly, the dental pin provides less stress contact with the tooth. Also, the dental pin is properly seated in the tooth. At the same time, the hand manipulation thereof permits the dentist to back off the dental pin within the bore in the tooth, thereby releasing a few thread turns after an improper insertion. In this manner, adequate control of the proper positioning of the dental pin can be achieved manually as determined by the dentist.

Numerous alterations of the structures herein disclosed will suggest themselves to those skilled in the art. However, it is to be understood that the present disclosure relates to preferred embodiments of the invention which are for purposes of illustration only and are not to be construed as limitations of the invention.

What is claimed is:

1. A placement assembly for a threaded dental pin, said assembly being receivable in a dental handpiece for insertion of the threaded dental pin into a preformed bore in a tooth, said assembly comprising:

a central elongated manipulating body portion;

a threaded dental pin projecting from an operating end of said body portion;

a shank frangibly coupled to a driving end of said body portion for driving engagement with the dental handpiece to thread said dental pin into the bore, said shank automatically severing from said body portion prior to a final seating of said dental pin;

said body portion including hand manipulation means for the final seating of the dental pin after severance of said shank; and disengagement means for retaining said dental pin in said operating end during said driving engagement and final seating thereof, and for permitting disengagement of said dental pin from said operating end after said final seating to leave said dental pin inserted in the bore.

2. A placement assembly as in claim 1, wherein said assembly is of unitary construction.

3. A placement assembly as in claim 1, wherein said dental pin includes a threaded post extending from an enlarged head, said head being disposed within said operating end of said body portion.

4. A placement assembly as in claim 3, wherein said operating end includes an annular shoulder beneath said head to provide said disengagement means for retaining said head within said body portion, said shoulder being deformable upon application of an axial disengaging force to release said dental pin from said body portion.

5. A placement assembly as in claim 3, wherein said head is captured in said operating end of said body portion, and said operating end has a mating configuration with said head.

6. A placement assembly as in claim 5, wherein said head has a slot, and a mating driving tang is provided in said operating end for driving said dental pin.

7. A placement assembly as in claim 5, wherein said head has a socket, and a mating socket driver portion is provided in said operating end for driving said dental pin.

8. A placement assembly as in claim 5, wherein said head has a square configuration, and a mating square seat is provided in said operating end for driving engagement with said head.

9. A placement assembly as in claim 5, wherein said head has a hexagonal configuration, and a mating hexagonal seat is provided in said operating end for driving engagement with said head.

10. A placement assembly as in claim 5, wherein said head has a D-shaped configuration, and a mating seat is provided in said operating end for driving engagement with said head.

11. A placement assembly as in claim 5, wherein said head has a double D-shaped configuration with opposing flat sides, and a mating seat is provided in said operating end for driving engagement with said head.

12. A placement assembly as in claim 5, wherein a periphery of said head is scalloped, and a mating slat is provided in said operating end for engagement with said head.

13. A placement assembly as in claim 5, wherein said operating end has an axial hole with a smaller mouth, a plurality of spaced apart axial slits extending through walls of said operating end surrounding said axial hole to facilitate disengagement of said body portion from said dental pin, a periphery of said head being scalloped with crests of said scallops being received within corresponding ones of said slits.

14. A placement assembly as in claim 1, wherein an inwardly tapered neck portion interconnects said shank with said body portion, said neck portion terminating in a reduced diameter frangible throat at a juncture with said body portion.

15. A placement assembly as in claim 1, wherein said body portion including a cylindrical knob portion with a depending stem portion, said knob portion providing said hand manipulation means.

16. A placement assembly as in claim 15, wherein a periphery of said knob portion is knurled to facilitate hand manipulation of said body portion.

17. A placement assembly as in claim 1, wherein latch drive means is provided at a distal end of said shank for engaging a latching mechanism of the dental handpiece.

18. A placement assembly as in claim 1, wherein said shank and body portion are of integral plastic construction, and said dental pin is of metal construction.

19. A placement assembly as in claim 1, wherein said operating end is bifurcated to provide a pair of opposing legs for disengagingly receiving a head of said dental pin therebetween.

20. A placement assembly as in claim 19, wherein an annular collar slidably surrounds said operating end for sliding over said bifurcated legs to clamp said legs together onto said head of said dental pin.

21. A placement assembly as in claim 19, wherein said legs are orthogonally bifurcated to define quadralateral legs.

22. A placement assembly as in claim 19, wherein said head of said dental pin includes a tang portion insertable between said bifurcated legs.

23. A placement assembly as in claim 22, wherein said tang portion is tapered to be wedgingly engaged between said bifurcated legs.

* * * * *